(12) United States Patent
Arano et al.

(10) Patent No.: US 7,354,567 B2
(45) Date of Patent: Apr. 8, 2008

(54) METHOD OF ENCAPSULATING METAL COMPLEX WITHIN LIPOSOMES

(75) Inventors: Yasushi Arano, Chiba (JP); Emi Kaneko, Chiba (JP); Masahiro Murakami, Osaka (JP)

(73) Assignee: Bio Med Core Incorporation, Aichi (JP)

( * ) Notice: Subject to any disclaimer, the term of this patent is extended or adjusted under 35 U.S.C. 154(b) by 387 days.

(21) Appl. No.: 10/503,139

(22) PCT Filed: Feb. 25, 2003

(86) PCT No.: PCT/JP03/02034

§ 371 (c)(1),
(2), (4) Date: Feb. 22, 2005

(87) PCT Pub. No.: WO03/072142

PCT Pub. Date: Sep. 4, 2003

(65) Prior Publication Data

US 2005/0129613 A1  Jun. 16, 2005

(30) Foreign Application Priority Data

Feb. 26, 2002 (JP) .............................. 2002-049037

(51) Int. Cl.
*A61K 51/00* (2006.01)
*A61M 36/14* (2006.01)
(52) U.S. Cl. ..................... 424/1.21; 424/1.11; 424/1.53
(58) Field of Classification Search ............... 424/1.11, 424/1.21
See application file for complete search history.

(56) References Cited

U.S. PATENT DOCUMENTS 4,925,650 A * 5/1990 Nosco et al. .............. 424/1.65
5,276,147 A * 1/1994 Thornback et al. .......... 534/14

FOREIGN PATENT DOCUMENTS

EP  0444130  6/1998

OTHER PUBLICATIONS

Oku et al., Nucl. Med. and Biol., 1993, 20, p. 407-412.*
W.T. Phillips et al., Nuclear Medicine and Biology, 1992, vol. 19, No. 5, pp. 539-543 and 545-547.
K. Kothari et al., Applied Radiation and Isotopes, 1993, vol. 44, No. 6, pp. 911-915.
G.F. Morgan et al., Journal of Nuclear Medicine, 1991, vol. 32, No. 3, pp. 500-505.

* cited by examiner

*Primary Examiner*—Michael G. Hartley
*Assistant Examiner*—Leah Schlientz
(74) *Attorney, Agent, or Firm*—Greenblum & Bernstein, P.L.C.

(57) ABSTRACT

An object of the present invention is to provide a method of producing liposome wherein a complex of a short half-life metallic radioactive nuclide such as $^{99m}$Tc and CD is encapsulated, with radiochemical yield and purity enabling practical application. The present invention provides a method of producing a liposome wherein a complex of a short half-life metallic radioactive nuclide and ethylenedicysteine (CD) is encapsulated, which comprises mixing a complex of a short half-life metallic radioactive nuclide and N-[2-(1H-pyrrolylmethyl)]-N'-(4-penten-3-on-2)-ethane-1,2-diamine with an ethylenedicysteine (CD)-encapsulated liposome, and incubating the mixture.

4 Claims, 10 Drawing Sheets

(A) direct encapsulating method (A) active loading

METHOD OF ENCAPSULATING METAL COMPLEX WITHIN LIPOSOMES

TECHNICAL FIELD

The present invention relates to a method of producing liposomes wherein a complex of a short half-life metallic radioactive nuclide such as $^{99m}$Tc and ethylenedicysteine (CD) is encapsulated. More specifically, the present invention relates to a method of producing liposomes wherein a complex of a short half-life metallic radioactive nuclide such as $^{99m}$Tc is encapsulated, by using a complex of a short half-life metallic radioactive nuclide such as $^{99m}$Tc coordinated with N-[2-(1H-pyrrolylmethyl)]-N'-(4-penten-3-on-2)-ethane-1,2-diamine, liposomes produced by said method, and a reagent kit for use in said method.

BACKGROUND ART

The diagnostic imaging of cancer using a radioactive nuclide allows a noninvasive early diagnosis of cancer. Technetium-99m ($^{99m}$Tc), a metallic radioisotope (RI), is the most suitable for clinical application among RIs commonly used for diagnostic imaging, since it has a half-life (6 hours) and a γ-ray energy (141 keV) suitable for diagnostic imaging and this nuclide is readily available as a physiology saline solution resulted from a generator system using $^{99}$Mo as a parent nuclide. There have been conducted many researches utilizing an antibody or a peptide as a labeling material for the purpose of selectively delivering $^{99m}$Tc to the tumor, and a liposome is also one of the carrier candidates for use in diagnostic imaging. A liposome is a closed vesicle composed of a lipid bilayer membrane. A liposome draws attention as a capsule type DDS carrier for a medicament such as chemotherapeutic drug, a protein, a nucleic acid, etc. Since liposomes can carry a large amount of radioactivity therein and also be formed target directed by the adjustment of particle size and chemical modification of the membrane surface, applications of $^{99m}$Tc-labeled liposomes to a high-sensitive diagnostic imaging of solid cancer, sentinel lymph-node and inflammation and infection sites are expected to be useful in nuclear medicine diagnosis as well.

It has been demonstrated that since tumor tissue has increased vascular permeability and lacks in recovery of substances via lymphatic system, macromolecules tend to infiltrate from the blood to the tumor interstitium and accumulate therein. It is also suggested by these properties that liposomes permeated into the tissue interstitium are not taken up into cells and rather stay in the cell interstitium in tumor tissue. Liposomes which circulate through a blood flow, however, are mainly captured by reticuloendothelial tissues such as liver or spleen, and are removed from the blood. Although liposomes wherein a nitrilotriacetic acid (NTA) complex of $^{67}$Ga and $^{111}$In is encapsulated have been well investigated as well for the purpose of diagnostic imaging of tumors and have exhibited excellent tumor accumulating properties in laboratory animals, they also exhibit high radioactivity accumulation in the liver and spleen, which has been a serious obstacle for practical application thereof. The liposomes incorporated into the liver and spleen are fused with lysosomes in the parenchymal cells, and are then metabolized. Encapsulated complexes of $^{67}$Ga and $^{111}$In-NTA released in the lysosomes at this time are water-soluble and cannot penetrate the membrane. The complexes decompose due to their low stability, and radioactive nuclides are accumulated in the lysosomes. This is supposed to the cause of the long-lasting radioactivity retention appearing in these tissues.

Accordingly, the present inventors considered that the non-specific retention of radioactivity would be dissipated by conferring properties to move from the lysosome into the blood and to be quickly excreted into the urine on the RI complexes released after liposomes are incorporated into the lysosomes in the cell and metabolized and released therefrom. $^{99m}$Tc-ethylendicysteine ($^{99m}$Tc-CD) (FIG. 1) has been selected as a complex having such properties. $^{99m}$Tc-CD has two molecules of free carboxylic acid and a stable pentavalent neutral complex structure. It is reported that $^{99m}$Tc-CD is excreted into the urine in a stable chemical form through the organic anion transporter in the kidney as in the case of para-aminohippuric acid. According to the researches of the present inventors, it has been demonstrated that when $^{186}$Re-CD, a CD complex of rhenium-186 ($^{186}$Re) which is a long half-life metallic radioactive nuclide of the same family as $^{99m}$Tc is encapsulated in the liposome, radioactivity accumulated in the liver and spleen can be promptly excreted into urine as $^{186}$Re-CD, and radioactivity retained in these internal organs can be significantly reduced. These results suggest that the radioactivity retained in the liver or spleen can be dissipated also with the use of liposomes wherein $^{99m}$Tc-CD complexes are encapsulated.

However, when a direct encapsulation approach was taken at the time of preparing $^{186}$Re-CD, where $^{186}$Re-CD complex is added to lipid as it is and then subjected to swelling, encapsulating efficiency is extremely low as 3.2%. Accordingly, it is necessary to establish a method of encapsulating $^{186}$Re-CD or $^{99m}$Tc into liposomes. Moreover, in case of clinical use, direct encapsulation approach requires liposomes to be prepared just before use. It is practically desired, however, that the liposomes prepared beforehand are labeled when clinically used. A technique has been reported as an efficient and simple encapsulating method for $^{67}$Ga and $^{111}$In, in which $^{67}$Ga and $^{111}$In-oxine complex having a high lipid solubility and substitution activity is prepared and is incubated with NTA-encapsulated liposomes so that the complex penetrates the liposome membrane and causes a ligand exchange reaction in the liposomes thereby retaining these nuclides as water-soluble chelate $^{67}$Ga and $^{111}$In-NTA within the liposomes (FIG. 2). When this encapsulating method called ligand exchange reaction is used, the encapsulation efficiency of $^{67}$Ga or $^{111}$In reaches to about 90%. Another technique for obtaining $^{99m}$Tc-labeled liposomes in high radiochemical yield comprises incubating $^{99m}$Tc-hexamethyl propyleneamine oxime ($^{99m}$Tc-HMPAO) which is a lipophilic complex with glutathione-encapsulated liposomes, thereby reductively converting the $^{99m}$Tc-HMPAO within the liposome into a water-soluble decomposed product. The encapsulating efficiency by this technique is about 60% to 90%. Recently, RI labeled liposomes used in nuclear medicine are most commonly prepared by this encapsulating method. This method, however, give rise to problems of radioactivity retention in the liver and spleen as mentioned above for each of the $^{67}$Ga, $^{111}$In and $^{99m}$Tc labeled liposomes.

DISCLOSURE OF THE INVENTION

The present invention aims at solving the above-mentioned problems of the prior art. Namely, not only increasing the encapsulation efficiency but also sufficiently improving the radiochemical purity of $^{99m}$Tc-CD within the liposome is necessary for achieving a prompt excretion of the administered radioactivity. Accordingly, an object of the present invention is to provide a method of producing liposome wherein a complex of a short half-life metallic radioactive nuclide such as $^{99m}$Tc and CD is encapsulated, with radiochemical yield and purity enabling practical application.

The present inventors intended to solve the above-mentioned problems and comparatively examined two types of $^{99m}$Tc complex having high membrane permeability and substitution activity, i.e. $^{99m}$Tc-HMPAO and $^{99m}$Tc-N-[2-(1H-pyrrolylmethyl)]-N'-(4-penten-3-on-2)-ethane-1,2-diamine (MRP20) (FIG. 3 by using them in the ligand exchange reaction. Furthermore, the present inventors investigated radiokinetics of the prepared $^{99m}$Tc-CD encapsulated liposomes, and evaluated the utility of the labeling method of the present invention in relation to diagnostic imaging by $^{99m}$Tc as well as internal radiotherapy with $^{186}$Re. Consequently, it has been found that $^{99m}$Tc-encapsulated liposomes which eliminate the non-specific retention of radioactivity in the liver and spleen can be prepared by encapsulating $^{99m}$Tc-CD in the liposomes by ligand exchange reaction utilizing $^{99m}$Tc-N-[2-(1H-pyrrolylmethyl)]-N'-(4-penten-3-on-2)-ethane-1,2-diamine ($^{99m}$Tc-MRP20). The present invention has been completed based on these findings.

That is, according to the present invention, there is provided a method of producing a liposome wherein a complex of a short half-life metallic radioactive nuclide and ethylenedicysteine (CD) is encapsulated, which comprises mixing a complex of a short half-life metallic radioactive nuclide and N-[2-(1H-pyrrolylmethyl)]-N'-(4-penten-3-on-2)-ethane-1,2-diamine with an ethylenedicysteine (CD)-encapsulated liposome, and incubating the mixture.

Preferably, there is provided a method of producing a $^{99m}$Tc-ethylenedicysteine (CD) complex-encapsulated liposome, which comprises mixing $^{99m}$Tc-N-[2-(1H-pyrrolylmethyl)]-N'-(4-penten-3-on-2)-ethane-1,2-diamine with an ethylenedicysteine (CD)-encapsulated liposome, and incubating the mixture.

According to another aspect of the present invention, there is provided a liposome wherein a complex of a short half-life metallic radioactive nuclide and ethylenedicysteine (CD) is encapsulated, which is produced by mixing a complex of a short half-life metallic radioactive nuclide and N-[2-(1H-pyrrolylmethyl)]-N'-(4-penten-3-on-2)-ethane-1,2-diamine with an ethylenedicysteine (CD)-encapsulated liposome, and incubating the mixture.

Preferably, there is provided a $^{99m}$Tc-ethylenedicysteine (CD) complex-encapsulated liposome, which is produced by mixing $^{99m}$Tc-N-[2-(1H-pyrrolylmethyl)]-N'-(4-penten-3-on-2)-ethane-1,2-diamine with an ethylenedicysteine (CD)-encapsulated liposome, and incubating the mixture.

According to a further another aspect of the present invention, there is provided a diagnostic or therapeutic agent which comprises the above-mentioned liposome.

According to a still further another aspect of the present invention, there is provided a reagent kit for use in the method of producing liposomes wherein a complex of a short half-life metallic radioactive nuclide and ethylenedicysteine (CD) is encapsulated according to the present invention, said kit comprising at least one substance selected from the group consisting of one or more liposome forming material; ethylenedicysteine (CD); ethylenedicysteine (CD) encapsulated liposome; a short half-life metallic radioactive nuclide; N-[2-(1H-pyrrolylmethyl)]-N'-(4-penten-3-on-2)-ethane-1,2-diamine; and a complex of a short half-life metallic radioactive nuclide and N-[2-(1H-pyrrolylmethyl)]-N'-(4-penten-3-on-2)-ethane-1,2-diamine.

Preferably, the short half-life metallic radioactive nuclide is $^{99m}$Tc or its salt.

BEST MODE FOR CARRYING OUT THE INVENTION

Figure 1:
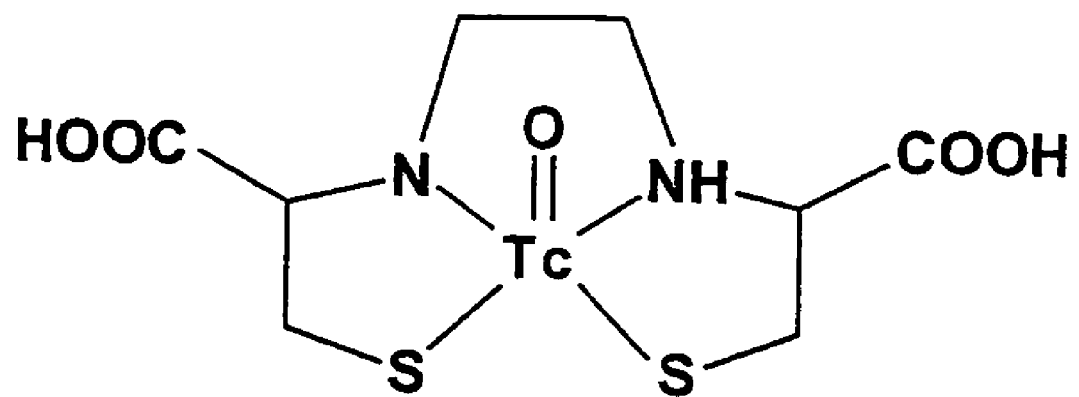
FIG. 1 shows the presumed structure of $^{99m}$Tc-CD. CD has nitrogen and sulfur as coordinating atoms, and forms a stable oxo-type complex with a pentavalent $^{99m}$Tc.
Figure 2:
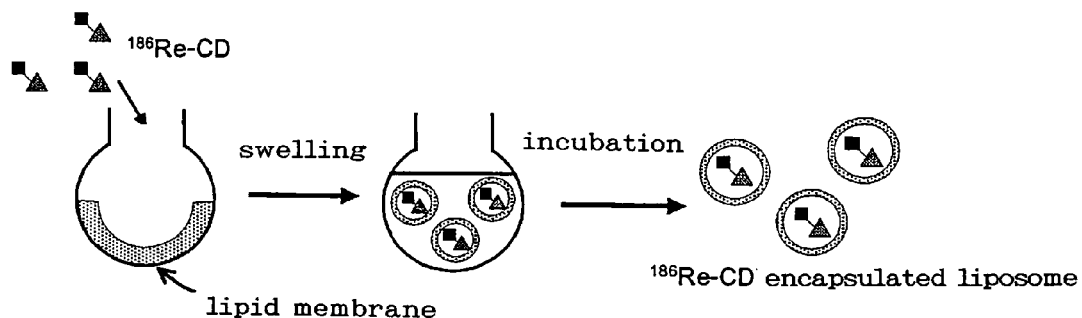
FIG. 2 shows a $^{86}$Re-CD direct encapsulating method (A) and a ligand exchanging reaction (B) by $^{111}$In-NTA;
■: CD, NTA
▲: $^{86}$Re or $^{111}$In
○: oxine
Figure 2:
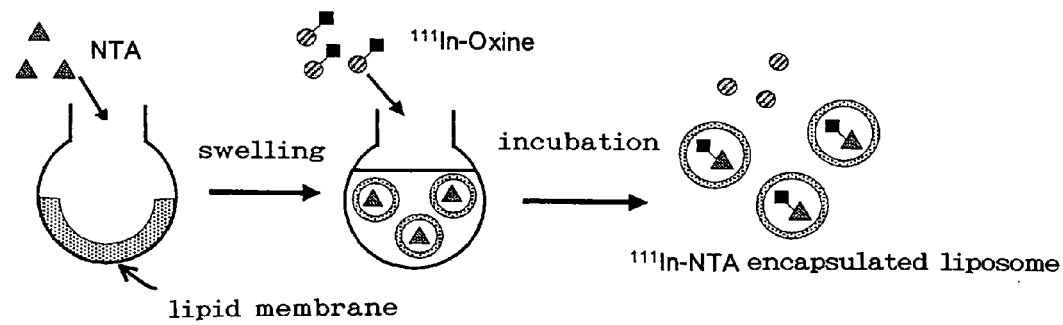
Figure 3:
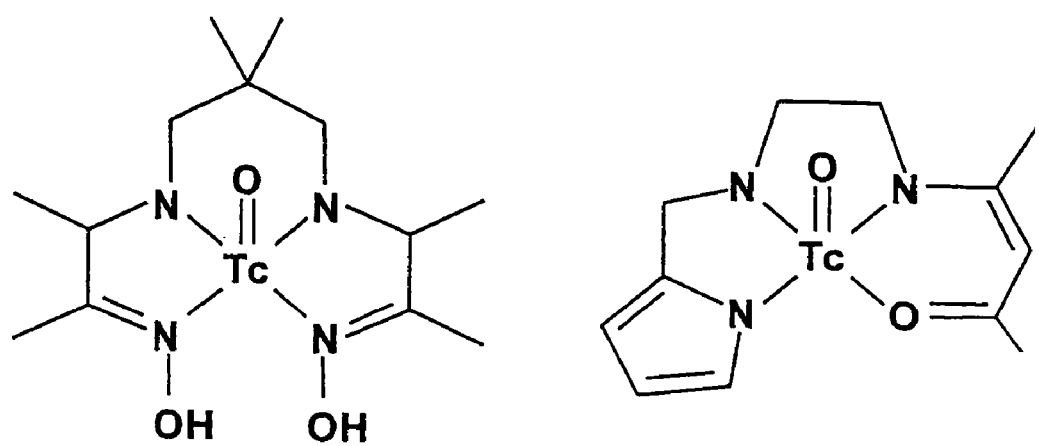
FIG. 3 shows structures of $^{99m}$Tc-HMPAO (left) and $^{99m}$Tc-MRP20 (right). They are $^{99m}$Tc complexes having high lipid solubility and substitution activity, and presumably they are relatively readily hydrolyzed and susceptible to ligand exchange reaction.

The mode for carrying out the present invention will be described below.

The method of producing a liposome wherein a complex of a short half-life metallic radioactive nuclide and ethylenedicysteine (CD) is encapsulated, which is provided by the present invention, is characterized in that it comprises mixing a complex of a short half-life metallic radioactive nuclide and N-[2-(1H-pyrrolylmethyl)]-N'-(4-penten-3-on-2)-ethane-1,2-diamine with an ethylenedicysteine (CD)-encapsulated liposome, and incubating the mixture.

Although the type of short half-life metallic radioactive nuclides which can be used in the present invention is not particularly limited, it is preferably $^{99m}$Tc (technetium 99m) or $^{186/188}$Re, and particularly preferably $^{99m}$Tc.

The complex of a short half-life metallic radioactive nuclide and N-[2-(1H-pyrrolylmethyl)]-N'-(4-penten-3-on-2)-ethane-1,2-diamine (MRP20), which is used in the present invention, can be prepared by mixing an ethanol solution of MRP20 and a hydrochloric acid solution of stannous chloride, adding a solution of $^{99m}$TcO$_4^-$ thereto and leaving the mixture at room temperature, for example, in the case that the short half-life metallic radioactive nuclide is $^{99m}$Tc. When a short half-life metallic radioactive nuclide other than $^{99m}$Tc is used, a solution containing the corresponding short half-life metallic radioactive nuclide may be used in place of the $^{99m}$TcO$_4^-$ solution.

The ethylenedicysteine (CD) encapsulated liposomes used in the present invention can be prepared by any conventional method using a liposome forming substance.

Although the liposome forming materials are not particularly limited as long as they are normally used in the art, but phospholipids and their derivatives and lipids other than phospholipids and their derivatives are preferably used for the purpose of providing liposomes stable in the living body.

Examples of the above-mentioned phospholipids include natural or synthetic phospholipids such as distearoylphosphatidylcholine, dipalmitoylphosphatidylcholine, dioleylphosphatidylcholine, phosphatidylcholine (lecithin), phosphatidylglycerol, phosphatidic acid, phosphatidylethanolamine, phosphatidylserine, phosphatidylinositol, sphingomyelin, cardiolipin, soybean lecithin and egg yolk lecithin, or those hydrogenated according to conventional methods.

Furthermore, the liposomes may be surface modified by adding a lipid derivative of a hydrophilic polymer. The lipid derivatives of a hydrophilic polymer which can be used are not particularly limited, as long as they do not impair the structural stability of liposome. Examples thereof include polyethyleneglycol, dextran, pullulan, ficoll, polyvinyl alcohol, synthetic poly amino acids, amylose, amylopectin, mannan, cyclodextrin, pectin, carragheenan, derivatives theirof, and the like. Particularly preferably, polyethyleneglycol and a polyethyleneglycol derivative can be used.

The liposomes used in the present invention may be used with a stabilizer, antioxidant, if needed. Examples of stabilizer include sterols such as cholesterol which reduces membrane mobility; sugars such as glycerol and sucrose, etc. Examples of antioxidant include tocopherol homologs, for example, vitamin E, etc.

In order to prepare liposome, liposome forming material, which may be a mixture of two or more types of material, dissolved in a solvent in the flask, may be evaporated under reduced pressure to remove the solvent to form a lipid thin membrane on the inner wall of the flask.

Any solvent can be used as long as it may dissolve the lipid used, and examples thereof include halogenated hydrocarbons such as chloroform, methyl chloroform and methylene chloride, hydrocarbons such as hexane and heptane, aromatic hydrocarbons such as benzene, toluene and xylene, ethers such as diethyl ether, diisopropyl ether, ethylene glycol dimethyl ether, tetrahydrofuran, etc.

Subsequently, after transferred to a vacuum desiccator to completely evaporate the solvent under a reduced pressure, the lipid may be added and swelled with a CD solution to obtain multilamellar liposomes (MLV) as a suspension. The liposomes may be further pressure filtered subsequently through membrane filters having a pore size such as 0.2 μm or 0.05 μm to form single membrane liposomes.

The obtained liposome dispersion liquid can be separated into liposomes and substances which have not been encapsulated in the liposomes by purification according to known methods such as gel filtration and centrifugal separation.

To the ethylenedicysteine (CD) encapsulated liposomes as obtained above, a complex of a short half-life metallic radioactive nuclide and N-[2-(1H-pyrrolylmethyl)]-N'-(4-penten-3-on-2)-ethane-1,2-diamine (particularly preferably $^{99m}$Tc-N-[2-(1H-pyrrolylmethyl)]-N'-(4-penten-3-on-2)-ethane-1,2-diamine, etc.) is added, and the mixture is incubated to produce liposomes wherein a complex of a short half-life metallic radioactive nuclide and ethylenedicysteine (CD) is encapsulated. The temperature and time of incubation are not particularly limited and can be set up suitably. For example, liposomes wherein a complex of a short half-life metallic radioactive nuclide and ethylenedicysteine (CD) is encapsulated can be prepared by carrying out incubation for 30 minutes to several hours at room temperature.

The liposomes wherein a complex of a short half-life metallic radioactive nuclide and ethylenedicysteine (CD) is encapsulated, which are obtained by the above-mentioned method of the present invention, are characterized by the high purity of the short half-life metallic radioactive nuclide (for example, $^{99m}$Tc)-CD complex. Since the radioactivity is expected to be dissipated from the liver or spleen more rapidly as the radiochemical purity of the short half-life metallic radioactive nuclide (for example, $^{99m}$Tc)-CD complex inside the liposome is high, the liposomes wherein a complex of a short half-life metallic radioactive nuclide and ethylenedicysteine (CD) is encapsulated, which is prepared by the method of the present invention, have characteristics that the radioactivity retained in the liver or spleen is extremely decreased as compared with conventional $^{99m}$Tc-encapsulated liposomes and $^{99m}$Tc-HMPAO-CD liposomes. Liposomes having such characteristics by themselves also fall within the scope of the present invention.

The liposomes wherein a complex of a short half-life metallic radioactive nuclide and ethylenedicysteine (CD) is encapsulated, which are obtained by the method of the present invention, are useful as a diagnostic or therapeutic agent for various diseases including cancer or tumor.

The liposomes of the present invention can be administered to a living body orally or parenterally. The administration method is preferably an administration by injection, and either one of intravenous, intramuscular, hypodermic and arterial injection, etc. can be used depending on the location of cancer or tumor, and intravenous injection is preferred.

When the liposomes of the present invention are administered as a diagnostic or therapeutic agent, the liposomes may be administered as they are, but they are administered in the form of a pharmaceutical composition containing the liposomes. The above-mentioned pharmaceutical composition comprises the liposomes of the present invention and a pharmaceutically accepted excipient and, if needed, may contain other pharmacological agents, carriers, auxiliary agents and the like.

When the liposomes of the present invention are administered by injection to a subject, they are preferably formed into a liquid pharmaceutical composition of a liquid.

The liquid pharmaceutical composition can be prepared as a solution or suspension, for example, by dissolving or dispersing the liposomes of the present invention in a carrier such as water, a physiology saline solution, aqueous glucose, glycerol, glycol or ethanol and, if needed, further adding an adjuvant thereto.

The pharmaceutical composition of the present invention may optionally contain a small amount of additives such as a wetting agent, an emulsifier, a solubilizing agent, and pH buffer agent (for example, acetate, sodium citrate, cyclodextrin derivatives, sorbitan monolaurate, triethanolamine sodium acetate). The method of preparing such a pharmaceutical composition is obvious to those skilled in the art.

Although the dosage of the liposomes of the present invention varies depending on the purpose of administration, type and amounts of the encapsulated short half-life metallic radioactive nuclide, etc., but typically they are administered in an amount of 0.1 mg to about 1 g for an adult patient.

Furthermore, in the present invention, $^{99m}$Tc-N-[2-(1H-pyrrolylmethyl)]-N'-(4-penten-3-on-2)-ethane-1,2-diamine ($^{99m}$Tc-MRP20) represented by the following formula is used:

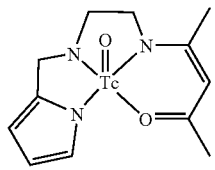

$^{99m}$Tc-MRP20 can be prepared by mixing a solution of N-[2-(1H-pyrrolylmethyl)]-N'-(4-penten-3-on-2)-ethane-1,2-diamine (MRP20) in ethanol and a solution of stannous chloride in hydrochloric acid, adding a solution of 99mTcO$_4^-$ thereto and leaving the mixture at room temperature.

Furthermore, the present invention provides a reagent kit for use in the method of producing liposomes wherein a complex of a short half-life metallic radioactive nuclide and ethylenedicysteine (CD) is encapsulated, said kit comprising at least one substance selected from the group consisting of one or more liposome forming material; ethylenedicysteine (CD); ethylenedicysteine (CD) encapsulated liposome ; a short half-life metallic radioactive nuclide; N-[2-(1H-pyrrolylmethyl)]-N'-(4-penten-3-on-2)-ethane-1,2-diamine; and a complex of a short half-life metallic radioactive nuclide and N-[2-(1H-pyrrolylmethyl)]-N'-(4-penten-3-on-2)-ethane-1,2-diamine.

The one or more liposome forming material and ethylenedicysteine (CD) in the above are reagents for preparing ethylenedicysteine (CD) encapsulated liposomes, and either one of them singly or the both may be contained in the reagent kit, or alternatively ethylenedicysteine (CD) encapsulated liposomes which was prepared may be contained in the reagent kit.

Similarly, a short half-life metallic radioactive nuclide and N-[2-(1H-pyrrolylmethyl)]-N'-(4-penten-3-on-2)-ethane-1,2-diamine are reagents for preparing a complex of a short half-life metallic radioactive nuclide and N-[2-(1H-pyrrolylmethyl)]-N'-(4-penten-3-on-2)-ethane-1,2-diamine, and either one of them singly or the both may be contained in the reagent kit, or alternatively a complex of a short half-life metallic radioactive nuclide and N-[2-(1H-pyrrolylmethyl)]-N'-(4-penten-3-on-2)-ethane-1,2-diamine which was prepared may be contained in the reagent kit.

The present invention will be described still more specifically by way of the following examples, but the present invention is not limited by these examples.

EXAMPLES

Materials and Method for Experiment

1. General Method

A physiology saline solution eluted from $^{99}$Mo/$^{99m}$Tc generator (Ultra Techne Kow, Daiichi Radioisotopes Laboratory) was used as a $^{99m}$TcO$_4^-$ solution. The product in the complex synthesis was confirmed by thin layer chromatography (TLC), paper chromatography (PC), cellulose acetate membrane electrophoresis method (EP) and reversed phase high performance liquid chromatography (RP-HPLC). TLC was developed with a mixed solvent (4:1) of chloroform and methanol using silica gel available from Merck (Silica gel 60 F$_{254}$). PC was developed with acetonitrile 50% using a filter paper available from Whatman (No. 1). EP was conducted using a cellulose acetate membrane (SELECA-V, Toyo Roshi Kaisha, Ltd.) for electrophoresis membrane, a veronal buffer solution (pH=8.6, I=0.06, Nacalai Tesque, Inc.) for buffer solution, a fixed current (1 mA/cm) for 25 minutes. RP-HPLC was conducted using COSMOSIL C$_{18}$-AR-300 column (4.6 mm×150 mm, Nacalai Tesque, Inc.) connected with a fraction collector (Pharmacia). All the collected fractions were measured with a gamma counter (ARC-380M, Aloka). The labeled compounds were analyzed at a flow rate of 0.5 ml/min and with a mobile phase of (A) 0.01M phosphate buffer solution (pH=7.0) and acetonitrile under the condition that the ratio of acetonitrile increased from 0 to 100% in 10 minutes, and (B) 0.0125M phosphate buffer solution (pH=2.5) and acetonitrile under the condition that the ratio of acetonitrile increased from 0 to 9% in 12 minutes and increased from 9 to 100% in 20 minutes to 40 minutes.

2. Synthesis of CD and MRP20

N,N'-Ethylenedicysteine (CD) was synthesized according to a method by Brondeau et al. (Blondeau et al. Canadian J Chem 45:49-52 and 1967). After an ammonia solution of L-thioproline (thiazolidine-4-carboxylic acid, Tokyo Kasei Kogyo Co., Ltd.) was added with metal sodium, NH$_4$Cl was added thereto, and the mixture was stirred overnight at room temperature. The generated crystals were dissolved in water and precipitated with hydrochloric acid (yield: 23%, melting point: 251 to 254° C.).

N-[2-(1H-pyrrolylmethyl)]-N'-(4-penten-3-one-2)-ethane-1,2-diamine (MRP20) was synthesized according to a method by Morgan et al. (Morgan et al. Inorg. Chim. Acta 190:257-264, 1991). Pyrrole-2-aldehyde and ethylen diamine were stirred in acetonitrile overnight, reduced with NaBH$_4$ in methanol solvent and extracted with chloroform under a basic condition to obtain an intermediate compound. Subsequently, the intermediate compound and acetyl acetone was stirred in acetonitrile, extracted with chloroform and purified by column chromatography using a silica gel column (solvent ethyl acetate: methanol=5:1) and recrystallization from benzene. Yield: 15.9%, melting point: 74 to 75° C. (document value of 75° C.).

3. Synthesis of $^{99m}$Tc-HMPAO and $^{99m}$Tc-MRP20

$^{99m}$Tc-HMPAO ($^{99m}$Tc-hexamethyl propyleneamine oxime) was prepared using a kit (Cerebrotec (registered trademark), Nycomed Amersham International) supplied from Nihon Medi-Physics Co., Ltd. $^{99m}$TcO$_4^-$ physiology saline solution was added to the kit, and it was used immediately after it was dissolved.

$^{99m}$Tc-MRP20 used was obtained by mixing 190 μl of a solution (17 mM) of MRP20 in ethanol and 10 μl of a 0.01N HCl solution (1.35 M) of stannous chloride, and adding 200 μl of $^{99m}$TcO$_4$$^-$ solution thereto and leaving the mixture at room temperature for 15 minutes.

Radiochemical yields of the obtained $^{99m}$Tc complexes ($^{99m}$Tc-HMPAO, $^{99m}$Tc-MRP20 and $^{99m}$Tc-CD) were determined by TLC, PC, EP and RP-HPLC. Determination of radiochemical yield was conducted by cutting the TLC plate, the filter paper, and the cellulose acetate membrane after dried into pieces of 5 mm width, subjecting each piece to measurement by gamma counter, and calculating the rate of the radioactivity at each Rf value assuming all the radioactivity of each plate as 100%.

4. Measurement of Partition Coefficient of HMPAO and MRP20

20 μl of HMPAO or MRP20 solutions adjusted to 8 mM with a physiology saline solution was added to 500 μl of octanol and 500 μl of a HEPES buffer solution (pH 7.0) or Na$_2$HPO$_4$—NaOH buffer solution (pH 12.0). The mixture was allowed to stand still after stirring. Absorption of the octanol layer and the aqueous layer was measured, and the lipophilic properties of the two complexes were compared.

5. Stability of $^{99m}$Tc Complex in an Aqueous Solution

In order to compare the stability of $^{99m}$Tc-HMPAO and $^{99m}$Tc-MRP20 in an aqueous solution, $^{99m}$Tc-HMPAO solution was diluted with 50 mM ammonia buffer solution (pH 9.4) into the final ligand concentration of 1 mM. The mixture was incubated in a water bath of 25° C. or 37° C., and radiochemical purity was determined by the above-mentioned analyzing methods after predetermined time (0.5, 2, 4, 8, or 24 hours). $^{99m}$Tc-MRP20 aqueous solution was diluted with 50 mM phosphate buffer solution (pH 8.3), and the similar operations were effected.

For the purpose of examining the effect of free ligands on the stability, $^{99m}$Tc complex solution was purified by RP-HPLC, and the purified $^{99m}$Tc complex solution eluted in 100% acetonitrile was mixed and diluted in the ratio of 1:1 with a buffer solution, and changes over time of the radiochemical purity of the complex was examined similarly as for the complex before purification.

6. Ligand Exchange Reactivity of $^{99m}$Tc Complex with CD

CD was dissolved in 1N NaOH to 66.7 mM, diluted with a buffer solution 10 times and pH adjusted with 2N HCl to obtain a CD solution. This CD solution, $^{99m}$Tc-HMPAO, and $^{99m}$Tc-MRP20 solution were mixed at a rate of 3:1, and after the mixture was incubated for 30 minutes at 37° C., radiochemical yield of Tc-CD was determined by EP. As a buffer solution to dilute CD, HEPES buffer solution (pH 7.0 or pH 8.3), an ammonia buffer solution (pH 9.4 or pH 10.5), and a sodium phosphate buffer solution (pH 11.2) (all 50 mM) were used. The CD concentration after mixing CD solution, $^{99m}$Tc-HMPAO, and $^{99m}$Tc-MRP20 solution was 5 mM, and HMPAO and MRP20 concentration was 2 mM.

7. Preparation of Liposome

After mixing and dissolving distearoyl phosphatidylcholine (DSPC, Nippon Oil & Fats) and cholesterol (CH, Sigma) at a ratio of 2:1 (15 μmole:7.5 μmole) in 2 ml of chloroform in an eggplant type flask, the solvents were evaporated at 65° C. under reduced pressure to form a thin film of lipid on the inner wall of the flask. After transferred to a vacuum desiccator to completely evaporate the solvent under reduced pressure for more than four hours, an almost isotonic aqueous solution of the substance to be encapsulated was added to swell the lipid at 65° C., thereby obtaining multilamellar liposomes (MLV) as a suspension. The liposomes were pressure filtered subsequently through membrane filters having a pore size such as 0.2 μm and 0.05 μm (Nuclepore (registered trademark) and Nomura Micro Science) to form single membrane liposomes (SUV). The thus generated liposomes were subjected to gel filtration having a carrier of Bio-Gel A-1.5 m (Bio-Rad) swelled with a 5% mannitol solution (EconoColumn, 1×30 cm, Bio-Rad) and eluted with a 5% mannitol solution for purification. Subsequently, the liposome solution was centrifuged at 400,000 g for 20 minutes, and the precipitate was resuspended with a physiology saline solution to prepare a liposome solution.

8. Preparation of $^{99m}$Tc-CD Encapsulated Liposome $^{99m}$Tc-CD encapsulated liposomes were prepared by ligand exchange reaction. CD was dissolved in a physiology saline solution, and pH was adjusted to 11.8 with 2N NaOH. 1.5 ml of the 5 mM CD solution was added to a thin membrane of phospholipid produced by the above-mentioned method, and after liposomes were prepared, non-encapsulated CD was removed by gel filtration. 500 μl of the resultant purified liposomes was diluted with the same volume of a physiology saline solution, and then 140 μl of $^{99m}$Tc-HMPAO and $^{99m}$Tc-MRP20 solutions were added thereto, and the mixture was incubated for 60 minutes at 37° C., and $^{99m}$Tc-CD encapsulated liposomes were obtained. The reaction solution was centrifuged, and the precipitated fraction was considered as a fraction of $^{99m}$Tc-CD encapsulated liposomes.

9. Preparation of $^{99m}$Tc/GSH Liposome $^{99m}$Tc/GSH liposomes were prepared according to the conventional method. GSH was dissolved in 135 mM NaCl/10 mM HEPES buffer (pH 7.4), and the pH was adjusted to pH=6.7 with 2N NaOH to prepare 50 mM GSH solution. After 1.5 ml of GSH solution was added to a thin membrane of phospholipid to prepare liposomes, non-encapsulated GSH was removed by gel filtration. 250 μl of $^{99m}$Tc-HMPAO was added to 500 μl of the purified liposomes, and the mixture was incubated for 40 minutes at 25° C., and $^{99m}$Tc/GSH liposomes were obtained. The reaction solution was centrifuged and the precipitated fraction was considered as a fraction of $^{99m}$Tc/GSH liposomes.

10. Analysis of the Contents of $^{99m}$Tc-CD Encapsulated Liposome

Each of the precipitate fractions of $^{99m}$Tc-CD liposome ($^{99m}$Tc-HMPAO-CD liposome) prepared with $^{99m}$Tc-HMPAO and $^{99m}$Tc-CD liposome ($^{99m}$Tc-MRP20-CD liposome) prepared with $^{99m}$Tc-MRP20 was added with ethanol in such a quantity to form about 250 kBq/ml solutions, and the mixtures were fully stirred and then allowed to stand additional for 20 minutes so as to dissolve the lipid membranes. The contents released from the liposomes were analyzed by EP.

11. Pharmacokinetics in a Normal Mouse $^{99m}$Tc-CD encapsulated liposome fraction or $^{99m}$Tc/GSH liposome fraction were diluted with a physiology saline solution so that the concentration of phospholipid might become 1.4 to 1.8 μmole/ml. 0.1 ml of each liposome solution was administered to a group of five ddY male mice of five-week old from the tail vein. The mice were sacrificed by decapitation in 10 minutes and 1, 3, 6 and 24 hours after administration, and each tissue was extracted and the weight and radioactivity as measured by gamma ray detection equipment of internal-organs were determined. The radioactivity distributed over each internal organs was expressed as radioactivity per 1 g of each internal organs (% ID/g tissue) assuming the total thereof as 100%.

The radioactivity in urine was analyzed 24 hours after administration. 300 µl of the collected urine was subjected to centrifugal filtration filter (Microcon (registered trademark), Millipore), and centrifugation was carried out at 4° C. at 8800 rpm for 15 minutes to remove proteins, and the resultant was filtered with 0.45-µm syringe filter and analyzed by EP and RP-HPLC.

Results

1. Chemical Properties of $^{99m}Tc$ Compounds $^{99m}TcO_4^-$ migrated 8.0 cm toward the anode side in EP, Rf value in TLC developed with a mixed solvent of chloroform and methanol was 0.8 to 0.9, and Rf value in PC developed with 50% acetonitrile was 0.9 to 1.0. $^{99m}TcO_2$ resulted by hydrolysis of reduced pentavalent $^{99m}Tc$ is considered to stay at the starting point in EP, TLC and PC. $^{99m}Tc$-CD migrated 6.0 cm toward the anode side in EP, and eluted after 22.0 minutes in RP-HPLC (B). $^{99m}Tc$-HMPAO did not migrate from the starting point in EP, and Rf value was 0.9 in TLC. Thus the radiochemical yield was determined by subtracting the rate of radioactivity attributable to $^{99m}TcO_4^-$ in EP from the rate of radioactivity at about 0.9 of TLC Rf value. The retention time in RP-HPLC (A) was 16.9 minutes. $^{99m}Tc$-MRP20 which was synthesized by the method shown below did not migrate from the starting point in EP, and exhibited Rf value of 0.8 to 1.0 in PC. Thus, the radiochemical yield was calculated by determining the rate of radioactivity retaining at the starting point in EP and the rate of radioactivity retaining at the starting point in PC. The retention time in RP-HPLC (A) was 18.1 minutes. These results (analysis value of $^{99m}Tc$ compounds) are summarized in Table 1.

chemical purity of $^{99m}Tc$-MRP20 after purified by RP-HPLC (A) was almost 100%.

4. Stability of $^{99m}Tc$ Complex in an Aqueous Solution

Figure 4:
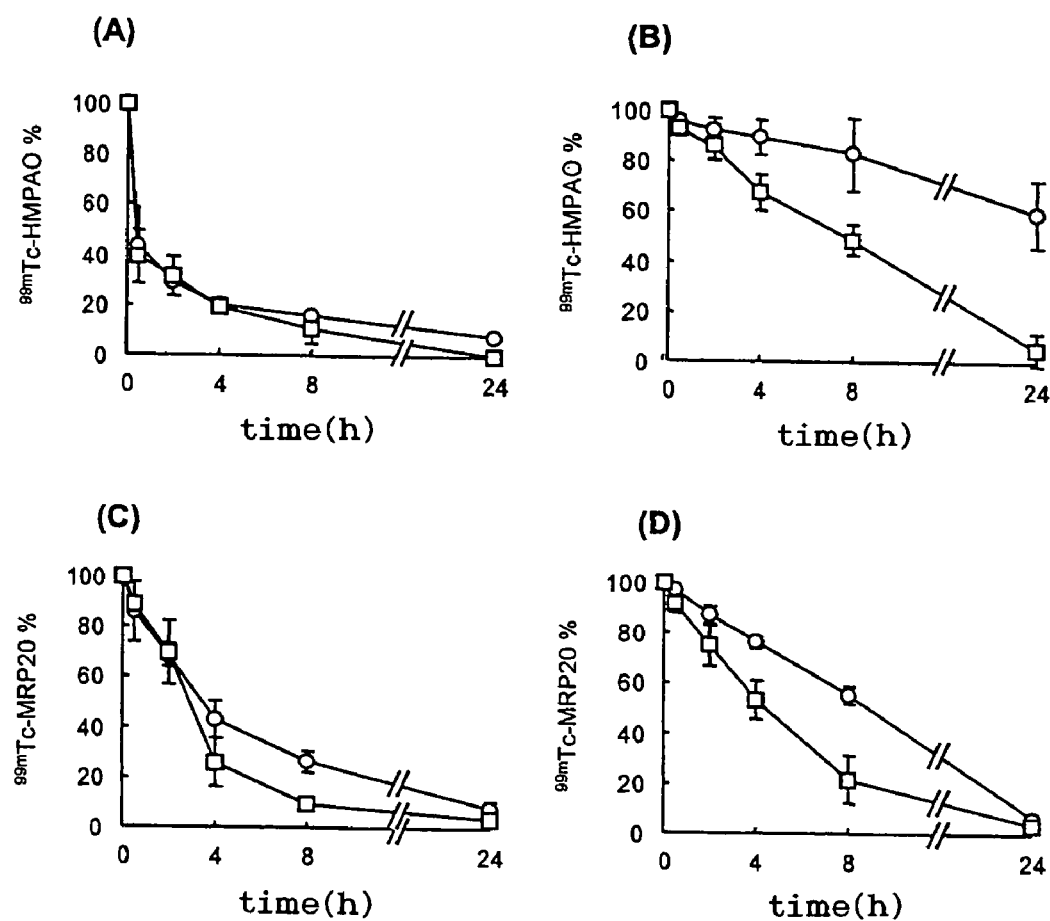
FIG. 4 shows stability of $^{99m}$Tc-HMPAO and $^{99m}$Tc-MRP20 in aqueous solutions. Changes over time of the radiochemical purity of each $^{99m}$Tc-complex are represented assuming that the purity is 100% at the 0-hour after the complexes are formed;
(A) $^{99m}$Tc-HMPAO before purified by RP-HPLC;
(B) $^{99m}$Tc-HMPAO after purified by RP-HPLC;
(C) $^{99m}$Tc-MRP20 before purified by RP-HPLC;
(D) $^{99m}$Tc-MRP20 after purified by RP-HPLC;
○: 25° C., □: 37° C.

Changes over time of the radiochemical purity of each complex present in the solution were examined for the complex solutions of $^{99m}Tc$-HMPAO and $^{99m}Tc$-MRP20 before and after purification by RP-HPLC. The results are shown in FIG. 4.

Unpurified $^{99m}Tc$-HMPAO was decomposed to about 40% in 30 minutes after complex formation, and continued to be decomposed relatively moderately. On the other hand, $^{99m}Tc$-MRP20 retained a radiochemical purity of about 70% even after 2 hours after the complex formation and was decomposed to about 40% at 25° C. at 4 hours after the complex formation. After purified, there were observed no significant differences between the stability of the two compounds at 37° C., and conversely, $^{99m}Tc$-HMPAO is more stable than $^{99m}Tc$-MRP20 at 25° C. After 24 hours, the radiochemical purity of $^{99m}Tc$-HMPAO was 59% whereas $^{99m}Tc$-MRP20 was decomposed to 6%.

5. Ligand Exchange Reactivity of $^{99m}Tc$ Complex with CD

Figure 5:
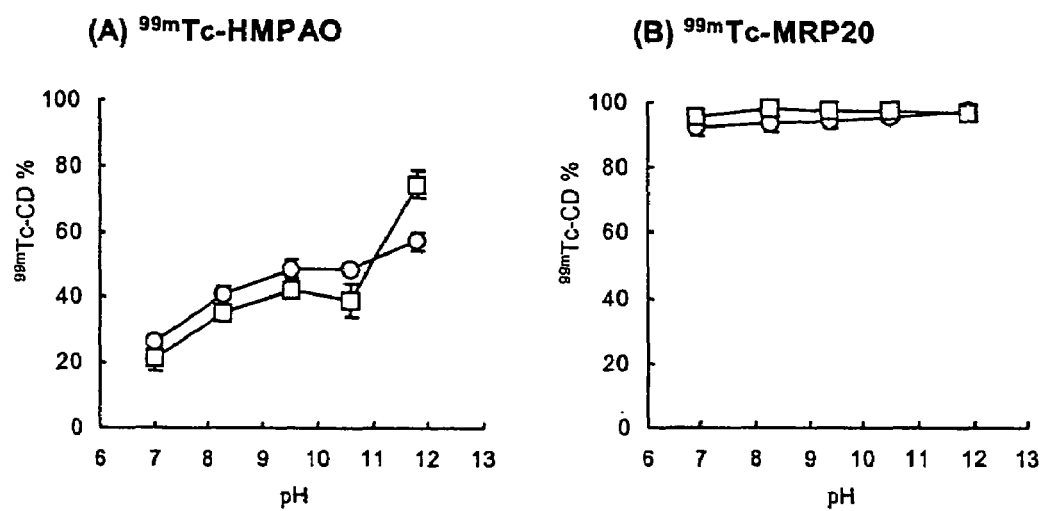
FIG. 5 shows the effect by pH on ligand exchange reactivity of $^{99m}$Tc-HMPAO (A) and $^{99m}$Tc-MRP20 (B), and CD. The radiochemical absorbance of $^{99m}$Tc-CD resulted from the exchange reaction is expressed on a vertical axis;
○: Exchange with $^{99m}$Tc-complexes before purified by RP-HPLC;
□: Exchange with $^{99m}$Tc-complexes after purified by RP-HPLC.

Effect of pH on the ligand exchange reactivity with CD was examined for both complexes of $^{99m}Tc$-HMPAO and $^{99m}Tc$-MRP20 before and after RP-HPLC purification. The results are shown in FIG. 5.

The yield of $^{99m}Tc$-CD in the exchange reaction between unpurified $^{99m}Tc$-HMPAO and CD increased as the pH of the mixture solution increased, and reached 57% at pH 11.9. Moreover, the yield or the rate of exchange reaction after purification also reached 74% at pH 11.9.

The ligand exchange reactivity between $^{99m}Tc$-MRP20 and CD was much higher than that of $^{99m}Tc$-HMPAO and CD, and exhibited $^{99m}Tc$-CD yield of 90% or more at a pH within the measurement range. Particularly, purified $^{99m}Tc$-MRP20 always showed 95% or more of $^{99m}Tc$-CD yield and did not affected by pH.

TABLE 1

| Analysis value of $^{99m}Tc$ compounds | | | | | |
|---|---|---|---|---|---|
| | $^{99m}TcO_4^-$ | $^{99m}TcO_2$ | $^{99m}Tc$-CD | $^{99m}Tc$-HMPAO | $^{99m}Tc$-MRP20 |
| TLC/CH$_3$Cl + MeOH Rf value | 0.8-0.9 | 0 | — | — | 0.9 |
| PC/50% CH$_3$CN Rf value | 0.9-1.0 | 0 | — | 0.8-1.0 | — |
| EP migration distance (cm) | 8.0 | 0 | 6.0-8.0 | 0 | 0 |
| RP-HPLC (A) retention time (min) | 4-5 | — | — | 18.1 | 16.9 |
| RP-HPLC (B) retention time (min) | 4-5 | — | 22.0 | — | — |

2. Partition Coefficient of HMPAO and MRP20

Absorbance of HMPAO transferred to the octanol layer was below the detection limit. The ratio of absorbances of MRP20 in the octanol layer and the water layer was 2.1±0.7 when the pH of the buffer was 7.0, and 5.0±1.6 when the pH was 12.0.

3. Synthesis of $^{99m}Tc$-MRP20

In the case that MRP20 was labeled with $^{99m}Tc$ by a conventional procedure, hydrolysis products of $^{99m}Tc$ having a negative charge were generated at 50% or more, and the yield of the labeled compound of interest was only about 35 to 40%. Accordingly, ethanol and hydrochloric acid (solvent) were purged with nitrogen for 6 hours or more, and tin/hydrochloric acid solution were added by small quantity to the reaction solution, and as result, $^{99m}Tc$-MRP20 was obtained by radiochemical yield of 81 to 92%. The radio- 6. Preparation of $^{99m}Tc$ Encapsulated Liposome Supernatant was sampled after $^{99m}Tc$ encapsulated liposomes were subjected to centrifugal separation, and encapsulation efficiency was determined by measuring the radioactivity of precipitation and supernatant respectively. Encapsulation efficiency was determined as the value obtained by dividing the radioactivity of precipitation by the sum of the radioactivity of precipitation and the radioactivity of supernatant. The encapsulation efficiency of $^{99m}Tc$-CD by the ligand exchange reaction using $^{99m}Tc$-HMPAO was 66.4% while the encapsulation efficiency of $^{99m}Tc$-CD using $^{99m}Tc$-MRP20 was 70.0%. The encapsulation efficiency to GSH liposome using $^{99m}Tc$-HMPAO was 75.1%.

Figure 6:
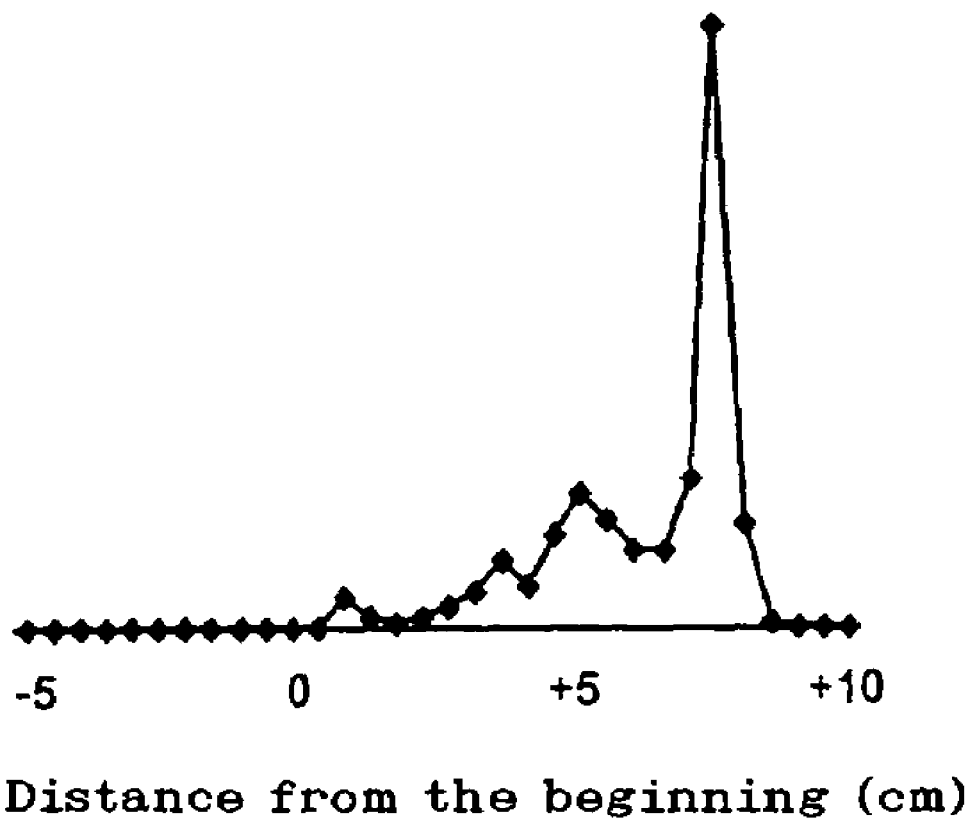
FIG. 6 shows EP analysis results of the contents of $^{99m}$Tc-CD liposome ($^{99m}$Tc (HMPAO)-CD liposome) prepared with $^{99m}$Tc-HMPAO.
Figure 7:
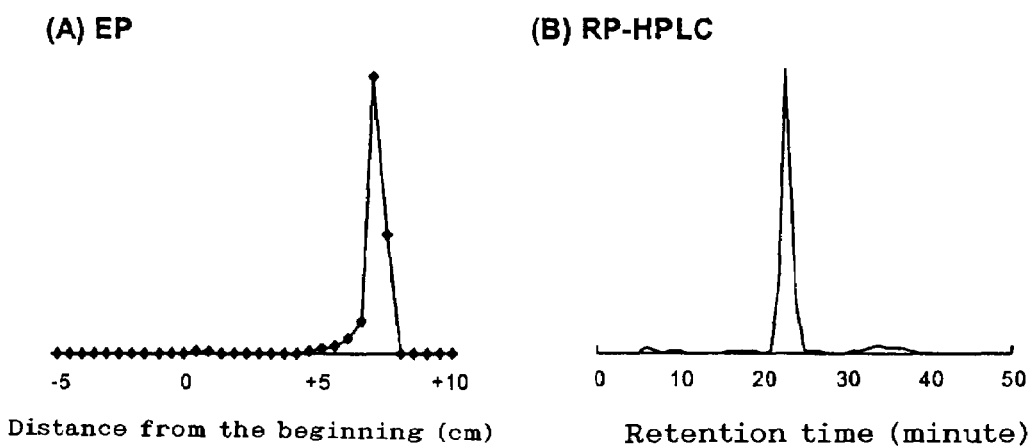
FIG. 7 shows EP analysis results (A) and RP-HPLC analysis results (B) of the contents of $^{99m}$Tc-CD liposome ($^{99m}$Tc(MRP20)-CD liposome) prepared with $^{99m}$Tc-MRP20.

The contents of $^{99m}Tc$-CD encapsulated liposomes were analyzed. The results are shown in FIGS. 6 and 7. As for $^{99m}Tc$(HMPAO)-CD liposomes and $^{99m}Tc$(MRP20)-CD liposomes, main peaks of the contents appeared in the range from 7.5 cm to 8.0 cm toward the anode side in EP. However, the radioactivity attributable to the peak corresponding to $^{99m}$Tc-CD was only 54% of the total radioactivity inside the liposomes in case of $^{99m}$Tc(HMPAO)-CD liposomes. On the other hand, in case of the contents of $^{99m}$Tc(MRP20)-CD liposomes, 91.1% of radioactivity migrated 6.5 cm toward the anode side in EP, and almost all the radioactivity was eluted at a retention time of 22.3 minutes in RP-HPLC (B).

7. Pharmacokinetics in Normal Mouse

Figure 8:
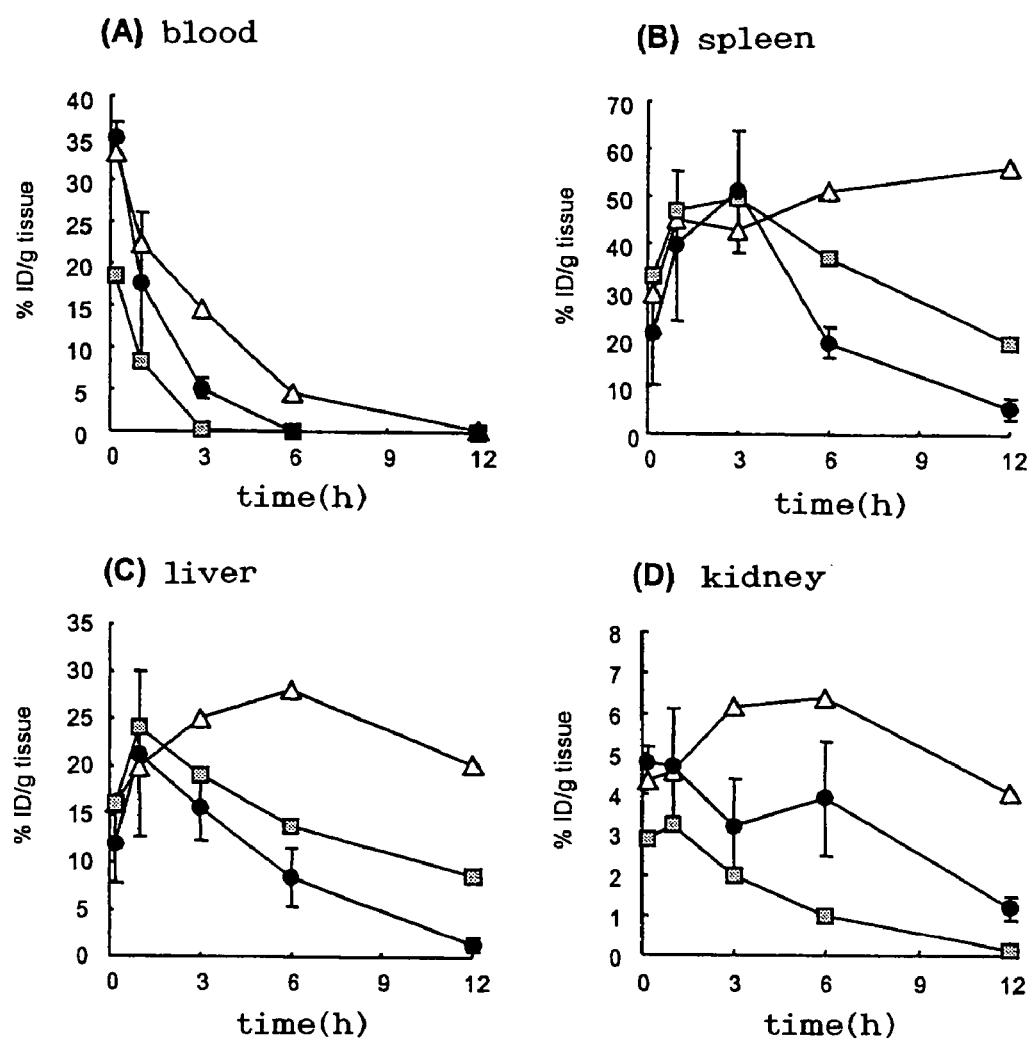
FIG. 8 shows radiokinetics of $^{99m}$Tc-labeled liposomes when intravenously administered to mice;
Δ: $^{99m}$Tc/GSH liposome;
■: $^{99m}$Tc(HMPAO)-CD liposome;
●: $^{99m}$Tc(MRP20)-CD liposome.

The radiokinetics in the living body is shown in FIG. 8, when $^{99m}$Tc-CD encapsulated liposomes labeled with $^{99m}$Tc-HMPAO or $^{99m}$Tc-MRP20, or $^{99m}$Tc/GSH liposomes used as comparative control, was intravenously administered to a normal mouse. The radioactivity disappeared from the blood to a similar extent in these three cases, and no significant difference was observed in the radioactivity accumulation in the liver or spleen at an early stage of administration. However, with the progress of time, increase in the radioactivity accumulation to these organs was observed in case of $^{99m}$Tc/GSH liposomes, and there arises a significant difference from the case of $^{99m}$Tc-CD liposomes in 6 hours. After 24 hours, 20% of the administered radioactivity was accumulated per 1 g of the liver, and the accumulation tendency of radioactivity was observed in spleen after 24 hours, and 56% of the administered radioactivity was remained. On the other hand, in the case of $^{99m}$Tc-CD encapsulated liposomes, the radioactivity in the liver and spleen peaked out at 30 minutes and 3 hours after administration respectively, and decreased with time thereafter. Moreover, when two types of $^{99m}$Tc-CD liposomes were compared, $^{99m}$Tc-MRP20-CD liposome showed more prompt radioactivity disappearance especially in 6 hours and 24 hours after administration, as compared with $^{99m}$Tc (HMPAO)-CD liposome.

Figure 9:
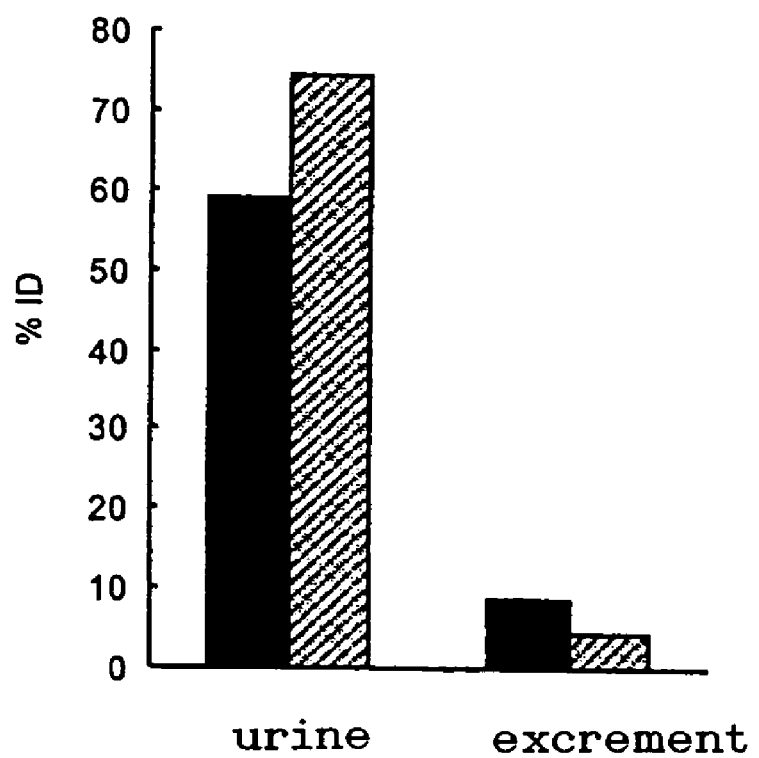
FIG. 9 shows the ratio of the radioactivity excreted out of the body to the administered radioactivity after $^{99m}$Tc-CD encapsulated liposomes are administered to mice; and
■: $^{99m}$Tc(HMPAO)-CD liposome administered group;
□(hatched): $^{99m}$Tc(MRP20)-CD liposome administered group.
Figure 10:
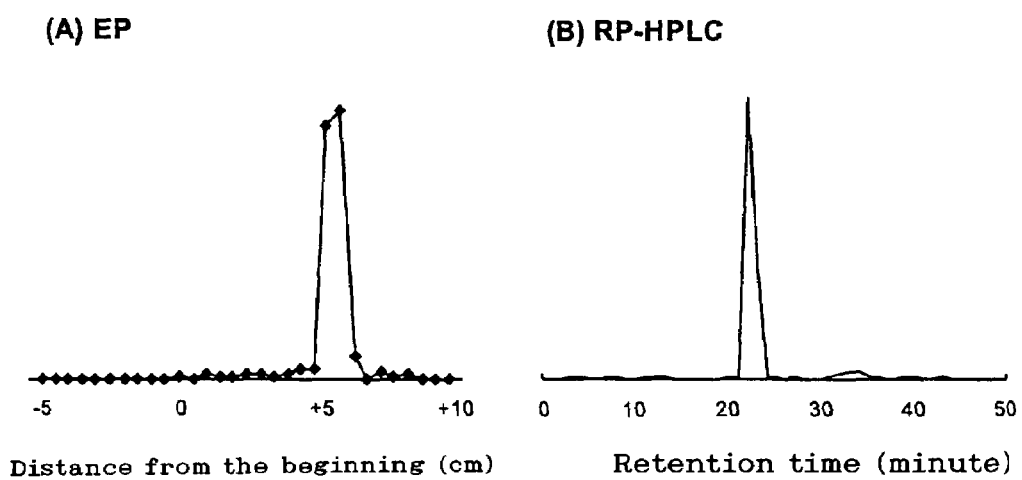
FIG. 10 shows the analysis results by EP (A) and RP-HPLC (B) of radioactivity which were excreted in urine after administering 99mTc(MRP20)-CD liposome to mice.

The amount of the radioactivity excreted out of the body in 24 hours after administration is shown in FIG. 9, and the results of analysis of the radioactivity in urine is shown in FIG. 10. The ratio of the radioactivity excreted into urine among the administrated radioactivity was 59% for $^{99m}$Tc (HMPAO)-CD liposomes administered group and 74% for $^{99m}$Tc(MRP20)-CD liposomes administered group. 91.2% of the radioactivity excreted in the urine after $^{99m}$Tc (MRP20)-CD liposomes were administered, migrated 6.0 cm toward the anode side in EP, and was eluted at a retention time of 22.5 minutes in RP-HPLC (B).

Consideration

Encapsulation by $^{99m}$Tc-HMPAO and glutathione encapsulated liposomes most commonly used in $^{99m}$Tc labeling method of liposomes enables encapsulation at high efficiency. However, such $^{99m}$Tc encapsulated liposomes contain reduction-decomposed substances of $^{99m}$Tc-HMPAO, and non-specific radioactivity retention caused by accumulation of $^{99m}$Tc compounds in reticuloenodothelial system give rise to problems of degradation of the picture accuracy. On the other hand, although preparation of $^{99m}$Tc-CD liposomes by direct encapsulation is remarkably low in encapsulation efficiency and inferior in practicality, radiochemical purity of $^{99m}$Tc-CD encapsulated in the liposomes is about 100% theoretically, and in fact, it has been demonstrated from previous investigation that about 80% of the administered radioactivity is actually excreted into urine after it is administered to a mouse, exhibiting prompt radioactivity disappearance from non-target tissues. If application to diagnostic imaging is taken into consideration, it is necessary that high radiochemical purity comparable to the direct encapsulating method and high radiochemical yield comparable to the conventional labeling method are accomplished simultaneously.

When $^{99m}$Tc-CD encapsulated liposomes were prepared in this example according to the ligand exchange reaction using $^{99m}$Tc-HMPAO or $^{99m}$Tc-MRP20, the encapsulation efficiency which was 3.2% as achieved in direct encapsulating method using $^{186}$Re-CD has been improved greatly to the range from 66 to 70%. Although no significant difference in encapsulation efficiency was observed between the use of $^{99m}$Tc-HMPAO and $^{99m}$Tc-MRP20 as membrane permeable complexes, significant difference has been observed in radiochemical purity of $^{99m}$Tc-CD encapsulated in the liposomes after encapsulation. $^{99m}$Tc-CD purity in $^{99m}$Tc(HMPAO)-CD liposomes is much lower as compared with $^{99m}$Tc-MRP20. This is attributable to the generation of the radioactive compound having a negative charge which is considered to be hydrolyzed substances of $^{99m}$Tc-HMPAO. The complex used as starting materials in a ligand exchange reaction needs to have high substitution activity and should be comparatively highly unstable. Therefore the generation reaction of a complex to be made competes with the decomposition reaction of the complex used as the starting material. Which reaction advances in predominance strongly depends on the stability of the complex itself used as starting materials. However, not only the stability of the complex itself but also the ligand concentration in liposomes is presumably important. As is apparent from the partition coefficient of HMPAO and MRP20, free MRP20 is much more lipophilic than HMPAO. MRP20 out of the membrane easily permeates through the liposome membrane by passive diffusion, thereby exhibiting a high concentration of free MRP20 inside the liposomes, and there is a possibility that the co-existence of resulted free ligands in excessive amount may bring forth a state where complexes are hardly hydrolyzed. Moreover, it is shown that $^{99m}$Tc-MRP20 itself has a higher stability than that of $^{99m}$Tc-HMPAO (FIG. 4) and that it is a complex having a high reactivity with CD (FIG. 5). It is considered that these factors work in favor of a ligand exchange reaction with CD and that $^{99m}$Tc-CD also generates in high purity within liposome.

Since the prompt radioactivity disappearance from the liver or spleen can be expected as the radiochemical purity of $^{99m}$Tc-CD inside liposomes is high. Accordingly the reason why $^{99m}$Tc-MRP20-CD liposome has reduced the radioactivity retention in the liver or spleen more significantly than conventional $^{99m}$Tc encapsulated liposomes and $^{99m}$Tc-HMPAO-CD liposomes is supposed to be the result that the purity of inner $^{99m}$Tc-CD gave a significant effect on the distribution of the radioactivity in the body after administration. This is also supported by the fact that 74% of the administered radioactivity was excreted into the urine and 91% thereof was detected with the chemical form of $^{99m}$Tc-CD. These results have revealed that ligand exchanging reaction using $^{99m}$Tc-MRP20 enables the production of high radiochemical yield of $^{99m}$Tc-CD encapsulated liposomes which reduces non-specific radioactivity retention involved in conventional method. The encapsulating method of the present invention is useful to produce $^{99m}$Tc labeled liposomes which enables high precision diagnostic imaging. Moreover, it is expected that the encapsulating method of the present invention gives fundamental knowledge for the production of cell killing $^{186/188}$Re labeled liposome for the purpose of inner radiotherapy for cancers.

INDUSTRIAL APPLICABILITY

Since $^{99m}$Tc-MRP20 which is a membrane permeable complex can give $^{99m}$Tc-CD in high yield through a ligand exchange reaction with CD, the ligand exchange reaction using $^{99m}$Tc-MRP20 according to the present invention enables production of $^{99m}$Tc-CD encapsulated liposomes at high radiochemical yield and high purity. Moreover, it has been demonstrated that $^{99m}$Tc-CD encapsulated liposomes produced by the present method greatly reduces the non-specific radioactivity retention in the liver and spleen involved in conventional method. Thus, the present invention enables to improve diagnostic imaging accuracy using $^{99m}$Tc labeled liposomes. Moreover, the method of the present invention is also applicable to the production of cell-killing $^{186/188}$Re labeled liposomes for the purpose of inner radiotherapy of cancers.

The invention claimed is:

1. A method of producing a liposome wherein a complex of a short half-life metallic radioactive nuclide and ethylenedicysteine (CD) is encapsulated, which comprises mixing a complex of a short half-life metallic radioactive nuclide and N-[2-(1H-pyrrolylmethyl)]-N'-(4-penten-3-on-2)-ethane-1,2-diamine with an ethylenedicysteine (CD)-encapsulated liposome, and incubating the mixture.

2. A method of producing a $^{99m}$Tc-ethylenedicysteine (CD) complex-encapsulated liposome, which comprises mixing $^{99m}$Tc-N-[2-(1H-pyrrolylmethyl)]-N'-(4-penten-3-on-2)-ethane-1,2-diamine with an ethylenedicysteine (CD)-encapsulated liposome, and incubating the mixture.

3. A reagent kit for use in the method of producing liposomes wherein a complex of a short half-life metallic radioactive nuclide and ethylenedicystein (CD) is encapsulated according to claim 1, said kit comprising ethylenedicysteine (CD) encapsulated liposome and a complex of a short half-life metallic radioactive nuclide and N-[2-(1H-pyrrolylmethyl)]-N'-(4-penten-3-on-2)-ethane-1,2-diamine.

4. The reagent kit of claim 3 wherein the short half-life metallic radioactive nuclide is $^{99m}$Tc or its salt.

* * * * *